(12) United States Patent
Signaevsky et al.

(10) Patent No.: US 11,538,947 B2
(45) Date of Patent: Dec. 27, 2022

(54) MULTILAYERED COMPOSITE MATERIAL UTILIZING QUANTUM DOT BASED PHOTOVOLTAIC EFFECT FOR BI-DIRECTIONAL BRAIN-COMPUTER INTERFACE

(71) Applicant: NeuroSilica, Inc., Wilmington, DE (US)

(72) Inventors: Maxim Signaevsky, Brookyin, NY (US); Igor Yehuda Yaroslavsky, Vancouver (CA)

(73) Assignee: NEUROSILICA, INC., Wilmington, DE (US)

( * ) Notice: Subject to any disclaimer, the term of this patent is extended or adjusted under 35 U.S.C. 154(b) by 376 days.

(21) Appl. No.: 16/685,260

(22) Filed: Nov. 15, 2019

(65) Prior Publication Data

US 2020/0161485 A1    May 21, 2020

Related U.S. Application Data

(60) Provisional application No. 62/768,558, filed on Nov. 16, 2018.

(51) Int. Cl.
*H01L 31/04* (2014.01)
*H01L 31/0352* (2006.01)
(Continued)

(52) U.S. Cl.
CPC ........ *H01L 31/035218* (2013.01); *A61B 5/24* (2021.01); *A61B 5/263* (2021.01); *A61B 5/6868* (2013.01); *C01B 32/158* (2017.08); *C01B 32/16* (2017.08); *G01H 11/08* (2013.01); *A61N 1/0534* (2013.01); *C01B 2202/08* (2013.01)

(58) Field of Classification Search
CPC ............ H01L 31/035218; H01L 31/04; H01L 51/0048
See application file for complete search history.

(56) References Cited

U.S. PATENT DOCUMENTS 8,013,359 B2    9/2011 Pettit
2004/0238887 A1*  12/2004 Nihey .................... B82Y 10/00
                                                    257/77
(Continued)

FOREIGN PATENT DOCUMENTS

WO    2012/003348 A2    1/2012

OTHER PUBLICATIONS

International Search Report and Written Opinion issued in International Application No. PCT/UC2019/061874, dated Jan. 23, 2020, pp. 1-8.

*Primary Examiner* — Hoa (Holly) Le
(74) *Attorney, Agent, or Firm* — Tutunjian & Bitetto, P.C.

(57) ABSTRACT

A photovoltaic unit that includes a biological interface for sensing an electrical signal from the biological tissue, the biological interface including a multilayered piezoelectric amplifier including a composite impulse generating layer including a matrix of a piezo polymeric material and dispersed phases including piezo nanocrystals and carbon nanotubes. The photovoltaic unit also includes a transducer structure comprising a fiber substrate having quantum dots present on a receiving end of the fiber. The receiving end of the fiber receiving the electrical signal. The quantum dots converts the electrical signal to a light signal.

7 Claims, 6 Drawing Sheets

(51) Int. Cl.
*G01H 11/08* (2006.01)
*C01B 32/16* (2017.01)
*A61B 5/24* (2021.01)
*A61B 5/00* (2006.01)
*C01B 32/158* (2017.01)
*A61B 5/263* (2021.01)
*A61N 1/05* (2006.01)

(56) References Cited

U.S. PATENT DOCUMENTS

| | | | |
|---|---|---|---|
| 2006/0145326 A1 | 7/2006 | Tran | |
| 2012/0073992 A1* | 3/2012 | Kim | B82Y 15/00 |
| | | | 257/E51.023 |
| 2013/0183660 A1* | 7/2013 | Yu | A61B 5/00 |
| | | | 205/792 |
| 2013/0322891 A1* | 12/2013 | Howe | G02B 6/1221 |
| | | | 385/101 |
| 2014/0319461 A1* | 10/2014 | Park | H01L 27/305 |
| | | | 257/14 |
| 2016/0035956 A1* | 2/2016 | Carroll | H01L 35/22 |
| | | | 136/205 |

\* cited by examiner

MULTILAYERED COMPOSITE MATERIAL UTILIZING QUANTUM DOT BASED PHOTOVOLTAIC EFFECT FOR BI-DIRECTIONAL BRAIN-COMPUTER INTERFACE

BACKGROUND

Technical Field

The present invention generally relates to interfaces with biological tissues, and more particularly to composite materials including quantum dot based photovoltaic effects for providing interfaces with biological tissues.

DESCRIPTION OF THE RELATED ART

The effect of electric impulses on nervous system has been attracting attention of doctors and researchers to develop new treatment approaches in neuromodulation, neurostimulation, neuroprosthetics, and brain-computer interface. Neurostimulation has been gained acceptance and popularity in a form of deep brain stimulation (DBS) for Parkinson's disease (PD).

Since first introduction, deep brain stimulation (DBS) has been approved as an effective treatment for variety of neurodegenerative diseases (ND), chronic pain, psychiatric disorders, and dystonias. Many neurodegenerative diseases (ND) (e.g. Alzheimer's disease (AD), Parkinson's disease (PD), amyotrophic lateral sclerosis (ALS), etc.) occur when neurons begin to deteriorate, lose their function and eventually die. This results in severe deterioration of mental capacity and/or physical functions, which leads to disability and death. Neurodegeneration is not solely limited to seniors. Chronic traumatic encephalopathy has been found in combat veterans and contact sport athletes.

Deep brain stimulation (DBS) is a neurosurgical procedure involving implantation of a medical device, which sends electrical impulses, usually through implanted electrodes, to specific target areas in the brain for the treatment of neurodegenerative diseases (ND) with proven long-term effect. Neurostimulation of the motor system is designed to improve quality of life of the paralyzed for various reason including trauma.

Even though, a significant improvement has been achieved with in the field of neurostimulation for the variety of diseases (e.g. neurodegenerative, demyelinating, post-traumatic); the interaction of medical devices for treatment and diagnostics with the brain and therefore is efficacy and safety has been an area of significant challenge for decades.

SUMMARY

In some embodiments, methods, compositions and structures that are described herein provide for biological tissue-to-electronic device interfaces that utilize a quantum dot based photovoltaic effect. The basis of the concepts disclosed herein is a combination of quantum dots impregnated into nano-porous glass fibers on front end of the fiber-optic cable, carbon nanotube "electron funnels" and a multilayered piezoelectric amplifier. In some embodiments, these features may be integrated into a photovoltaic unit. In one embodiment, the photovoltaic unit includes a biological interface for sensing an electrical signal from the biological tissue. In some embodiments, the biological interface can be connected to a biological interface. The biological interface being a layer that touches a type of biological tissue, such as the brain. The biological interface may include a multilayered piezoelectric amplifier including a composite impulse generating layer including a matrix of a piezo polymeric material and dispersed phases including piezo nanocrystals and carbon nanotubes; carbon nanotube funnels for receiving the electrical signal from the biological interface; and a transducer structure comprising a fiber substrate having quantum dots present on a receiving end of the fiber substrate, the receiving end of the fiber receiving the electrical signal from the carbon nanotube funnels, the quantum dots converting the electrical signal to a light signal, which is further propagated along the fiber substrate.

The multilayered piezoelectric amplifier may be a component of a biological surface interface material and can include at least one composite electrical impulse generating layer comprising a matrix phase of a piezo polymer material, a first dispersed phase of piezo nanocrystals, and second dispersed phase of carbon nanotubes, the first and second dispersed phase presented through the matrix phase. The piezo polymer material and piezo nanocrystal convert mechanical motion into electrical impulses and accept electrons to charge the composite impulse generating layer, and the carbon nanotubes provide pathways for distribution of the electrical impulses.

In another aspect, the photovoltaic unit may be employed in a method of interfacing with a biological tissue. In one embodiment, the method of interfacing with the biological tissue may include sensing an electrical signal from the biological tissue with a biological interface including a multilayered piezoelectric amplifier including a composite impulse generating layer including a matrix of a piezo polymeric material and dispersed phases including piezo nanocrystals and carbon nanotubes. In a following step, the method can further include receiving the electrical signal from the biological interface with carbon nanotube funnels; and converting the electrical signal to a light signal with a transducer structure. In some embodiments, the transducer structure includes a fiber substrate having quantum dots present on a receiving end of the fiber substrate. The receiving end of the fiber receives the electrical signal from the carbon nanotube funnels, and the quantum dots providing said converting of the electrical signal to the light signal.

In another aspect of the present disclosure, a two dimensional multi-layered piezoelectric amplifier structure is provided that includes dispersed phases of piezo nanocrystals and carbon nanotube funnels. The two dimensional multi-layered piezoelectric amplifier structure may be an interface structure for a biological environment. In one embodiment, the interface structure to the biological environment may include at least one composite electrical impulse generating layer comprising a matrix phase of a piezo polymer material, a first dispersed phase of piezo nanocrystals, and a second dispersed phase of carbon nanotube funnels, wherein the first and second dispersed phases are present throughout the matrix phase. The piezo polymer material and piezo nanocrystal convert mechanical motion into electrical impulses and accept electrons to charge the composite impulse generating layer. The carbon nanotube funnels provide pathways for distribution of the electrical impulses to a transmission surface of the composite impulse generating layer, and delivery of byproducts of free radical degradation from the biological environment to both piezo-nanocrystals and piezo-polymer material.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Methods, systems and compositions are provided herein that employ quantum dot and fiber-optic based technology, and a set of devices based on this technology. In some embodiments, the methods systems and computer program products that are described herein can provide a multichannel bi-directional broadband high-density signal exchange interface between the brain, or other excitable tissue targets and the computing devices.

The technology is designed for acquiring/receiving/sensing electric impulses from the brain and/or spinal cord and transmitting them to electronic devices, as well as delivering impulses from electronic devices to the target areas of the brain/spinal cord.

Figure 1:
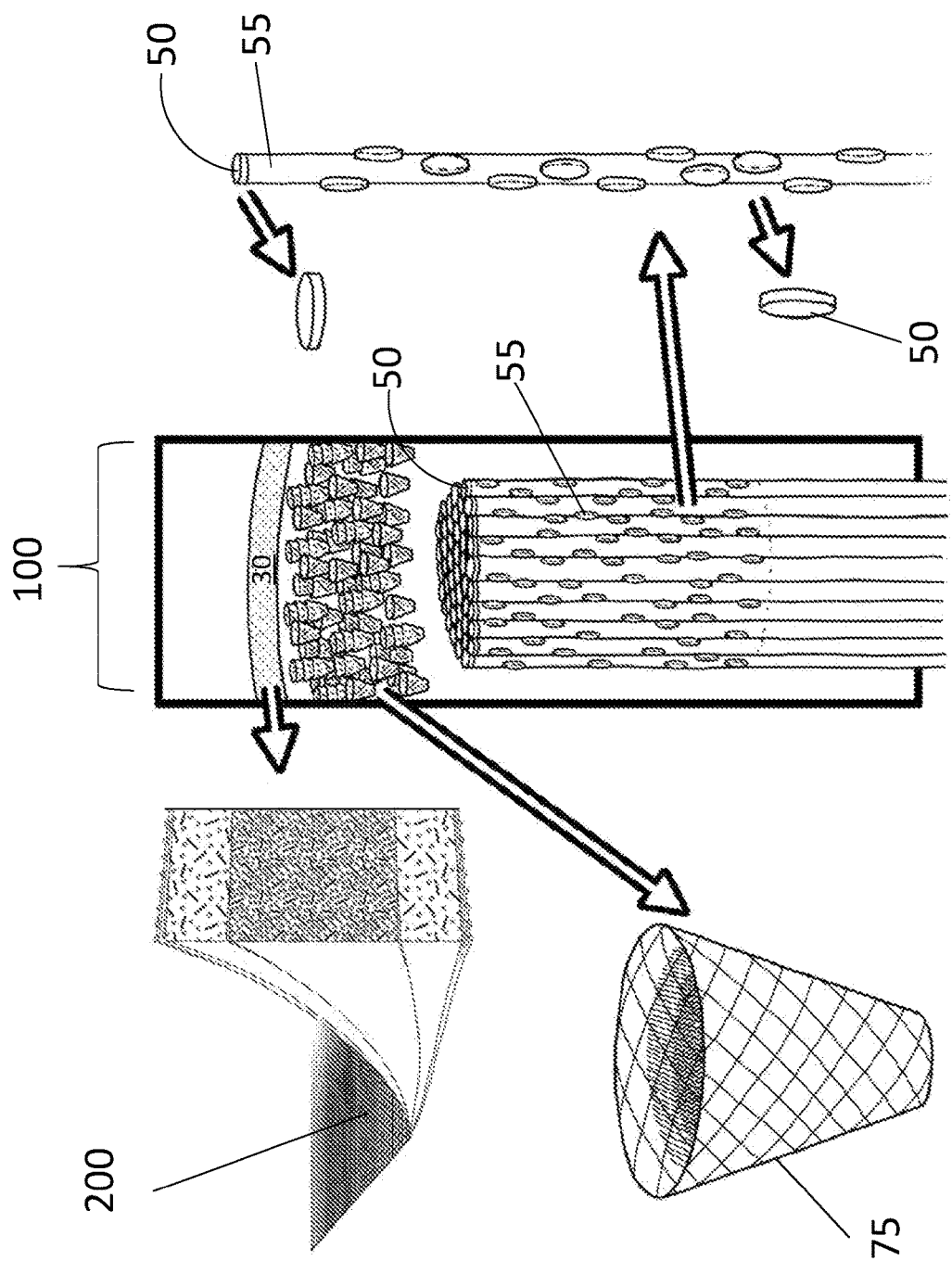
FIG. 1 is a perspective view of a photovoltaic unit including a plurality of fiber substrates, e.g., optical fibers, embedded with quantum dots, in accordance with one embodiment of the present disclosure.

FIG. 1 depicts a photovoltaic unit 100 including a biological interface 30 and a plurality of fiber substrates 55, e.g., optical fibers, embedded with quantum dots 50. In FIG. 1, the structure identified by reference number 50 is a cluster of quantum dots. It is noted that the fiber substrates 55 are hereafter referred to as being optical fibers 55. However, this is only one embodiment of the disclosure, and the fiber substrates 55 are not limited to only being optical fibers.

In one embodiment, the biological interface 30 is provided by a multilayered piezoelectric amplifier 200. The multilayered piezoelectric amplifier 200 can sense electric signal from a biological tissue, e.g., the cellular membrane of a neuron, as well as amplify the electric signal using the piezoelectric effect of the multilayered piezoelectric amplifier 200. When the photovoltaic unit 100 is employed to send a signal, the electrical signal can be distributed to the surrounding biological tissue, e.g., neurons, via the biological interface 30, which includes the including a multilayered piezoelectric amplifier 200.

In some embodiments, the plurality of optical fibers 55 of the photovoltaic unit 100 includes a first end of the optical fibers 55 at the interface end of the photovoltaic unit 100, in which the first end of the optical fibers 55 are embedded with quantum dots 50. As depicted in FIG. 1, at least one quantum dot 50 is present on the front end of the optical fiber 55, which is closest to the biological interface 20, and quantum dots 50 may be randomly positioned on the sides of the optical fiber 55. The portions of the optical fiber 55 that include the quantum dots 50 can convert an electrical signal to a light signal, and vice versa, depending on whether the photovoltaic unit is functioned to sense a signal or to deliver a signal. The back end of the optical fiber 55 may not include quantum dots 50 and can provide the transmission portion of the fiber optic cable. In some embodiments, the front ends of the optical fiber 55 are glued together with the optical glue. As depicted in FIG. 1, the whole structure forms a cylinder with the embedded quantum dots 50 on the front end, and the fiber optic cable on the back end. The function of the front end is to transform electrons into photons in one direction, and photons into electrons in another direction due to photovoltaic phenomenon. The function of the back end is to transmit light to and from the front end.

Still referring to FIG. 1, in some embodiments, carbon nanotube funnels 75 may be positioned to provide the interface between the biological interface 30 that is provided by a multilayered piezoelectric amplifier 200 and the quantum dots 50 on the plurality of optical fibers 55 of the photovoltaic unit 100.

The basis of the structures described herein include receiving signals. More specifically, in one embodiment, an electric signal will be sensed from the cellular membrane of a neuron with a multilayered structure, such as the two dimensional structure 200 depicted in FIG. 2, further amplified with the use of the piezo-electric effect, and transported onto quantum dots 50 via carbon nanotube "funnels" 75. The impulses will be further amplified within these structures with the use of the piezo-electric effect, and transported onto quantum dots via carbon nanotube "funnels". Quantum dots 50 will transform an amplified electric signal into light, which characteristics will depend on the composition of the particular quantum dot 50. The resulting light will be further passed to a hardware processing computer via fiber optics 55 for analysis.

Figure 2:
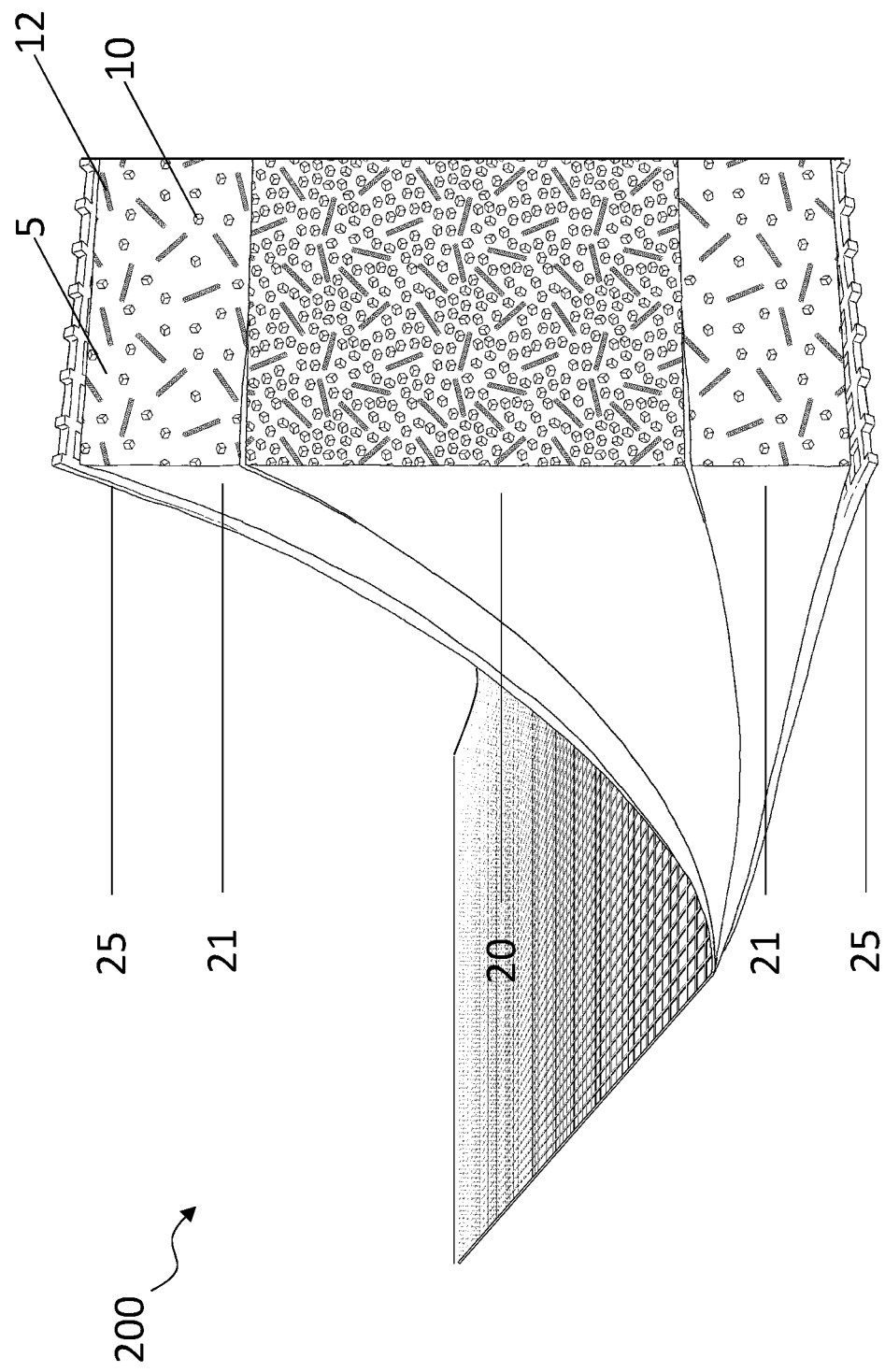
FIG. 2 is a perspective view of a two dimensional multi-layered piezoelectric amplifier structure to send and receive signals in which at least one layer of the two dimensional structure includes carbon nanotubes.

In some embodiments, for receiving impulses, e.g., signals, neuronal action potential (or a grading potential) in a form of an electric signal will be sensed/acquired from the cellular membrane of a neuron with a multilayered biological interface structures, herein referred to as a multilayered piezoelectric amplifier 200, and previously described in U.S. patent application Ser. No. 15/883,793. The entirety of U.S. patent application Ser. No. 15/883,793 is incorporated herein by reference. FIG. 2 illustrates one example of a multilayered biological interface structures, i.e., multilayered piezoelectric amplifier 200, described in U.S. patent application Ser. No. 15/883,793.

The basis of the structures described herein also include sending signals. For sending signal, a light signal from a coherent light source (i.e. LED, laser) will be sent to quantum dots 50 via fiber optics 55, where it will be transformed into electrical signals, in correspondence to the particular quantum dot 50. An electrical signal will be further distributed to the biological interface surface through polarized carbon nanotubes.

Figure 5:
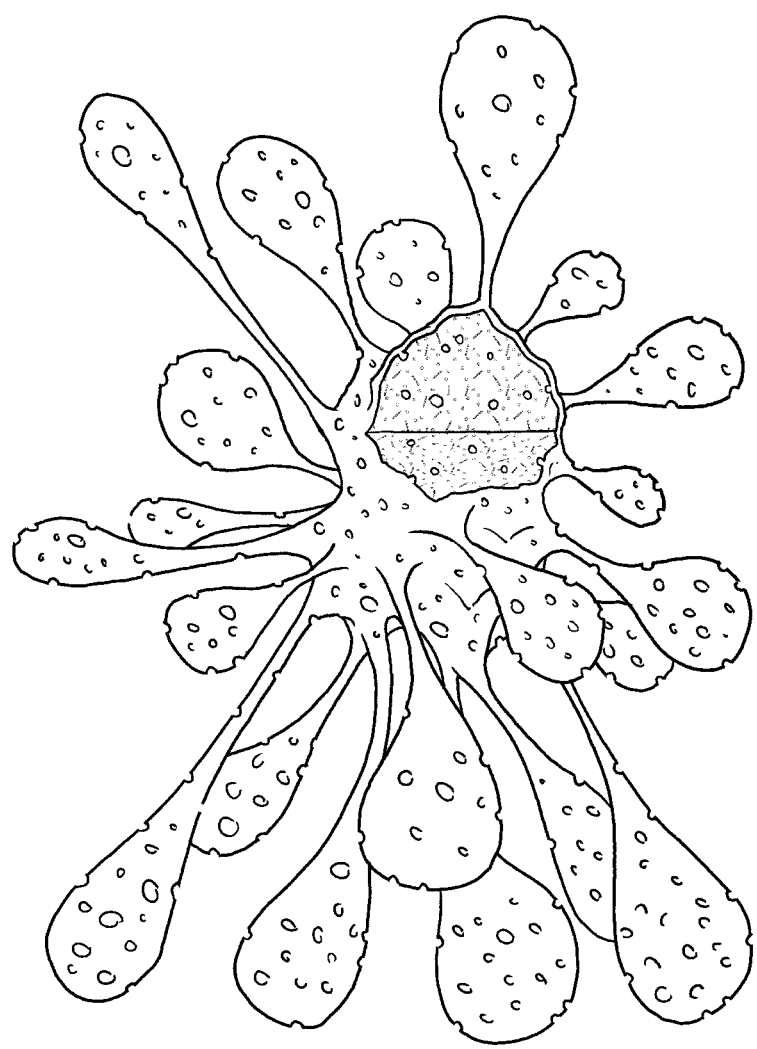
FIG. 5 is a second embodiment of a three dimension sponge used to send and receive signals, in which the photovoltaic unit depicted in FIG. 1 is integrated into the sponge configuration depicted in FIG. 5.

The system may further provide for analysis of signals and close-loop feedback. For example, a computing device/system, as depicted in FIG. 5, will be able operate both receiving from the brain and sending to the brain signals in an operational and a feedback manners, using operational software and a machine learning. The advanced feature of this system is that offers a high-density multichannel (high-density pixelated surface and various light wave lengths) signal exchange between the brain and computing devices. Thus, the proposed system allows a bi-directional interface between brain (neurons) and a computer.

The methods, systems and compositions are provide herein may be practiced as a modular system designed for reading/sensing electrical impulses from neurons, amplifying them with the multilayered amplifier (the multilayered piezoelectric amplifier 200), concentrating and pixelating them with the CNT funnels 75, transforming them with the array of quantum dots 50 into the light of various wavelength and intensity, and sending them along optical fibers 55, and being accepted with the light sensor/detector, and further to the computing devices.

The biological contact surface and the multilayered piezoelectric amplifier, which is referred to herein as a multilayered piezoelectric amplifier 200, has been described in U.S. patent application Ser. No. 15/883,793. An example of the structure that can provide the biological contact surface and the multilayered piezoelectric amplifier is depicted in FIG. 2. FIG. 2 depicts one embodiment of a two-dimensional structure/embodiment to send and receive signals. The multilayered sending/receiving/amplifying layer consists of biological environment interface layer 25. In some embodiments, the biological environmental interface 25 may be provided metal nano-particles embedded in the polymer, e.g. mixture of piezo-polymer and dielectric polymers; and/or a random distribution of nano metal dots and/or micro metal dots on the surface of the film/ribbon geometry form factor for the interface structure. It is noted that FIG. 2 only illustrates the outer layer, e.g., the biological surface interface. The CNTF funnels can go through this layer. In some embodiments, the CNTF funnels go beyond the biological interface to the quantum dots in the cylinder.

The multilayered piezoelectric amplifier 200 may include a composite electrical impulse generating layer 20 may include the piezo polymeric material 5 in an amount ranging from 70 wt. % to 84.9 wt. %; piezo nanocrystals 10 in an amount ranging from 15 wt. % to 30 wt. %; and carbon nanotubes 12 in an amount ranging from 0.1 wt. % to 1 wt. %. In one example, the piezo polymeric material 5 is present in the composite electrical impulse generating layer in an amount equal to 79.5 wt. %; the piezo crystal 10 are present in the composite electrical impulse generating layer 20 in an amount equal to 20 wt. % and the carbon nanotubes 12 are present in an amount that is equal to 0.5 wt. %.

The multilayered piezoelectric amplifier 200 may include a composite electrical impulse amplifying layer 21. The composite electrical impulse amplifying layer 21 is present between the composite impulse generating layer 20 and the biological environment interface layer 25. The composite electrical impulse amplifying layer 21 is similar in its composition to the composite impulse generating layer 20. For example, similar to the composite impulse generating layer 20, the composite impulse amplifying layer 21 may include a matrix phase of a piezo polymer material 5, a first dispersed phase of piezo nanocrystals 10, and second dispersed phase of carbon nanotubes 12, in which the first and second dispersed phase presented through the matrix phase. However, the concentration of piezo nanocrystals 10 in the composite electrical impulse amplifying layer 21 is higher than the concentration of the piezo nanocrystals 10 in the composite electrical impulse generating layer. In one embodiment, the composite impulse amplifying layer 21 may include the piezo polymer 5 in an amount ranging from 10 wt. % to 30 wt. %; the piezo nanocrystals 10 may be present in an amount ranging from 70 wt. % to 89.9 wt. %; and carbon nanotubes (CNTs) 11 in an amount ranging from 0.1 wt. % to 1.0 wt. %. In one example, the composite impulse amplifying layer 21 can include the piezo polymer material 5 in an amount equal to 24.5 wt. %, the nano crystals 10 in an amount equal to 70 wt. %, and the carbon nanotubes 11 may be present in an amount equal to 0.5 wt. %. For the purposes of comparison, the composite electrical impulse generating layer may include the piezo polymeric material 5 in an amount ranging from 70 wt. % to 84.9 wt. %; piezo nanocrystals 10 in an amount ranging from 15 wt. % to 30 wt. %; and carbon nanotubes 11 in an amount ranging from 0.1 wt. % to 1 wt. %.

The multilayered piezoelectric amplifier 200 can provide for piezo electric effects. Piezo-electric effects, i.e., piezoelectricity, is based on the ability of a material, e.g., crystal, to generate an electrical charge when mechanically loaded with pressure or tension, which is called the direct piezo effect. A piezoelectric polymer 5 is a material having piezoelectricity, i.e., the ability of material, which is the property that the polarization of a material change by applying stress and/or strain generated by changing polarization). The piezoelectric polymer 5 provides the matrix of a composite structure. A composite is a material composed of two or more distinct phases, e.g., matrix phase and dispersed phase, and having bulk properties different from those of any of the constituents by themselves. As used herein, the term "matrix phase" denotes the phase of the composite that is present in a majority of the composite, and contains the dispersed phase, and shares a load with it. In the present case, the matrix phase may be provided by a polymer.

The word "polymer" can be defined as a material made out of a large number of repeating units which are linked to each other through chemical bonding. A single polymer molecule may contain millions of small molecules or repeating units which are called monomers. Polymers are very large molecules having high molecular weights. Monomers should have a double bond or at least two functional groups in order to be arranged as a polymer. This double bond or two functional groups help the monomer to attach two more monomers, and these attached monomers also have functional groups to attract more monomers. A polymer is made in this way and this process is known as polymerization. The result of polymerization is a macromolecule or a polymer chain. These polymer chains can be arranged in different ways to make the molecular structure of a polymer. The arrangement can be amorphous or crystalline. The main difference between amorphous and crystalline polymers is their molecular arrangement. Amorphous polymers have no particular arrangement or a pattern whereas crystalline polymers are well arranged molecular structures. Further details on the piezoelectric polymer are provided below.

For example, the piezo polymer 5 that provides the matrix for the multilayered piezoelectric amplifier 200 may be polyvinylidene fluoride trifluoroethylene (PVDF-TrFE), which is a copolymer of PVDF. Polyvinylidene fluoride trifluoroethylene (PVDF-TrFE) can crystallize into β-phase directly from melt. In some embodiments, β-phase is thermodynamically favored for piezo-effect. In other examples, the piezo polymer material may have a composition that is selected from the group consisting of polyvinylidene flouride (PVDF), polyvinylidene fluoride (PVDF) copolymer with triflourethylene (TrFE), polyvinylidene fluoride (PVDF) copolymer with tetrafluoroethylene (TFE), polyvinylidene fluoride (PVDF) copolymer with tetrafluorethylene (TFE) and triflourethylene (TrFE), nylon 11, poly(vinylidenecyanide vinylacetate), and combinations thereof.

As noted above, piezoelectric electric generation, i.e., electric impulses are not only generated by the piezoelectric polymer 5, but are also generated by piezo nanocrystals 10 that are present as one dispersed phase of the multilayered piezoelectric amplifier 200. Crystalline solids or crystals, e.g., the piezo nanocrystals, have ordered structures and symmetry. The atoms, molecules, or ions in crystals are arranged in a particular manner; thus, have a long range order. In crystalline solids, there is a regular, repeating pattern; thus, we can identify a repeating unit.

In some embodiments, the piezo nanocrystal 10 is provided by a ceramic composition. Ceramics exhibiting piezo-electric properties can belong to the group of ferroelectric materials. One family of ceramic nanocrystals exhibiting piezo-electric properties include lead zirconate titanate (PZT); in which the members of this family consist of mixed crystals of lead zirconate ($PbZrO_3$) and lead titanate ($PbTiO_3$). Piezo-ceramic components have a polycrystalline structure comprising numerous crystallites (domains) each of which consists of a plurality of elementary cells. The elementary cells of these ferroelectric ceramics exhibit the perovskite crystal structure, which can generally be described by the structural formula $A^{2+}B^{4+}O_3^{2-}$. The piezo nanocrystals may also include niobium (Nb) based crystals.

The piezo nanocrystals 10 are of a nanoscale. "Nanoscale" denotes that the piezo nanocrystals have a cross-section width that is less than 500 nm. In some examples, the piezo nanocrystals have a cross-sectional width ranging from 20 nm to 100 nm.

The piezo nanocrystals 10 provide one dispersed phase of the composite, in which the matrix phase of the composite is provided by a piezo polymeric material. As used herein, the term "dispersed phase" denotes a second phase (or phases) that is embedded in the matrix phase of the composite. The dispersed phase may be present throughout an entirety of the material that provides the matrix.

In some embodiments, the piezo nanocrystal 10 can be composed of a piezo ceramic material. For example, the piezo ceramic material that provides the piezo nanocrystal may have a composition selected from the group consisting of lead zirconate ($PbZrO_3$), lead titanate ($PbTiO_3$), and combinations thereof. In one example, the material composition of the piezo nanocrystal 10 that is employed in the composite electrical impulse generating layer is a single-crystal piezoelectric $(1-\chi)PbZn_{1/3}Nb_{2/3}O_3$-$\chi PbTiO_3$ (PZNT) (further PMN-PT), which has a piezo-electric coupling coefficient (d33) up to 2500 pm/V, which is higher than that of conventional piezo-ceramics. For example, the piezoelectric coupling coefficient (d33) of single-crystal bulk PMN-PT is about 30 times higher than that of $BaTiO_3$, which is approximately 85.3 pm/V, and almost 4 times higher than that of PZT bulk material.

In another example, the material of the piezo nanocrystal 10 is Li-doped (K, Na)$NbO_3$ as a ceramic piezoelectric crystalline component. In yet another example, which may be suitable for long-term biocompatibility, lead free materials may be preferred. For example, the piezo nanocrystal 10 can be $Ba(Ce_xTi_{1-x}O_3)$, which is a mixture of Cerium-Barium Titanate (C-BT) with $(0.94(Bi_{0.5}Na_{0.5}TiO_3)+0.06(BaTiO_3))$ as a solid solution.

The first dispersed phase of piezo nanocrystals 10 may have a nanowire-type geometry, and in some instances can have a substantially spherical geometry. In the instances, in which the piezo nanocrystals 10 have a nanowire-type geometry, the piezo nanocrystals have a cross-sectional width ranging from 20 nm to 100 nm, and the length of the piezo nanocrystals 10 can range from 100 nm to 500 nm. The dimensions of the piezo nanocrystals 10 are provided for illustrative purposes only, and are not intended to limit the present disclosure to this example.

The composite also includes a second dispersed phase of carbon nanotubes 12. The carbon nanotubes 12 provide pathways for distribution of the electrical impulses to a surface of the composite impulse generating layer contacting the biological environment, and the delivery of free radicals from the biological environment to at least the piezo nanocrystals. "Nanotube" as used herein is meant to denote one form of nanostructure having an aspect ratio of length to width greater than 10. The term "nanotube" includes single wall and multi-wall nanotubes unless specifically specified as distinct. In one embodiment, a carbon nanotube is at least one graphene layer wrapped into a cylinder. In one embodiment, a single wall carbon nanotube 12 is a graphene rolled up into a seamless cylinder with diameter of the order of a nanometer. A multi-wall carbon nanotube 12 is a plurality of graphene sheets rolled up into a seamless cylinder with diameter of the order of a nanometer.

The carbon nanotubes (CNT) 12 within the multilayered piezoelectric amplifier 200 are cylindrical structures made of carbon with unique mechanical and electronic properties. Carbon nanotubes (CNTs) 12 are rolled up sheets of hexagonally ordered carbon atoms, giving tubes with diameters on the order of a few nanometers and lengths typically in the micrometer range. In some embodiments, the carbon nanotubes (CNT) 12 may be discrete. By discrete it is meant that they are singular in form and non-agglomerated. They may be single-walled or multiwalled (SWCNTs and MWCNTs respectively), and can be electrically conducting or semi-conducting depending upon the orientation of the carbon lattice with respect to the tube axis (known as chirality in this context). In some embodiments, the carbon nanotubes (CNTs) 12 are designed to haphazardly penetrate polymer matrix, i.e., piezo polymer material. The function of the carbon nanotubes (CNTs) 12 are to collect, conduct, and accept electrons and toxic free oxygen radicals in intercellular space $[O^{3-}+C+e=CO_2]$, including those generated as a result of electric impulses delivery.

The diameter of a single wall carbon nanotube may range from about 1 nanometer to about 400 nanometers. In another embodiment, the diameter of a single wall carbon nanotube may range from about 1.2 nanometers to about 1.6 nanometers. In one embodiment, the nanotubes 15 used in accordance with the present invention have an aspect ratio of length to diameter on the order of approximately 200:1 or greater. For example, the length of the carbon nanotubes (CNTs) may be as great as 1 mm.

Figure 3:
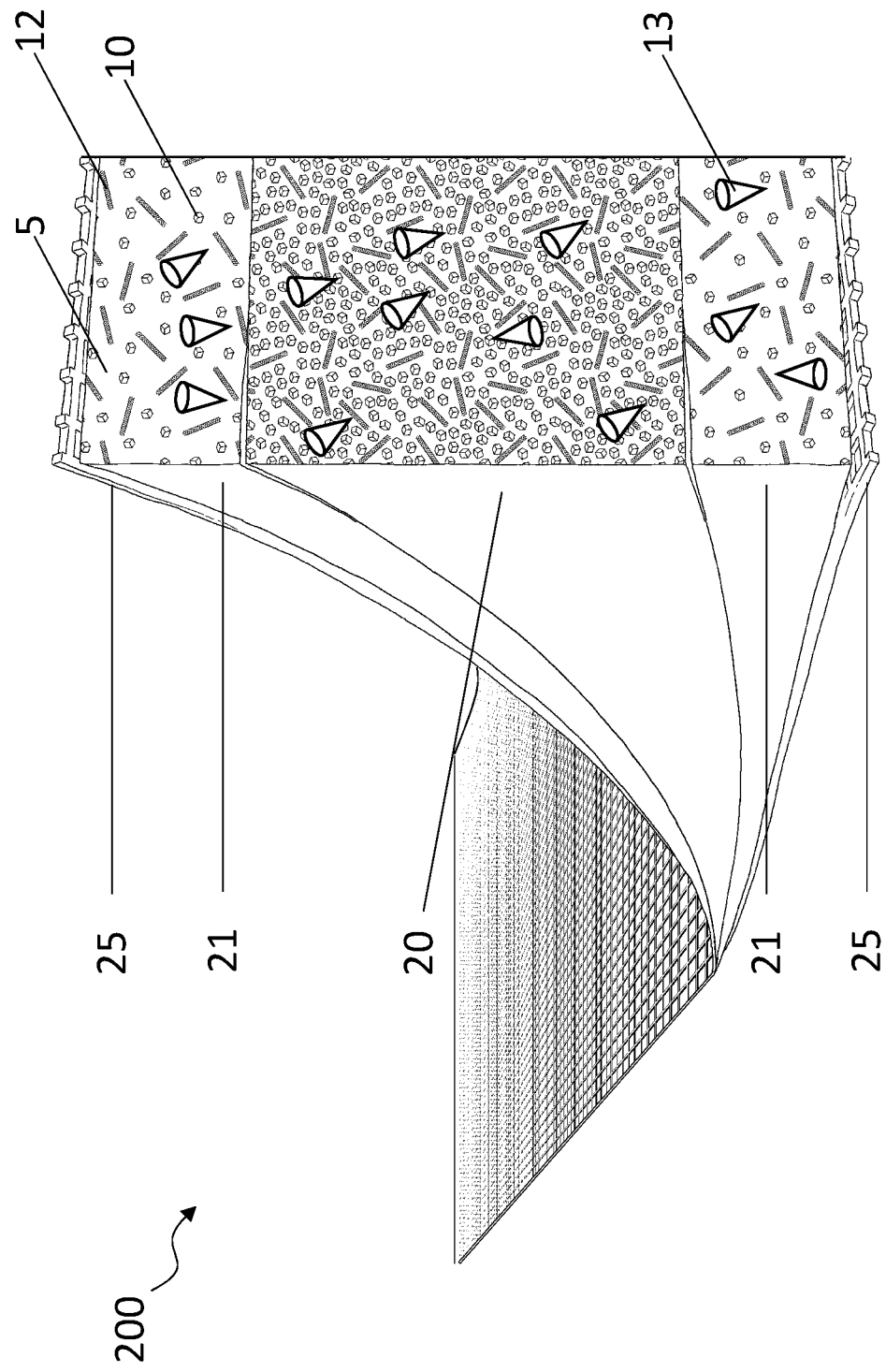
FIG. 3 is a perspective view of a two dimensional multi-layered piezoelectric amplifier structure to send and receive signals in which at least one layer of the two dimensional structure includes carbon nanotube funnels (CNTF).

However, in some embodiments, the geometry of the carbon nanotubes (CNT) may be in the form of funnels, i.e., carbon nanotube funnels 13. FIG. 3 is a perspective view of a two dimensional multi-layered piezoelectric amplifier structure to send and receive signals in which at least one layer of the two dimensional structure includes carbon nanotube funnels (CNTF) 13.

In another aspect of the present disclosure, a two dimensional multi-layered piezoelectric amplifier structure 200 is provided that includes dispersed phases of piezo nanocrystals 10 and carbon nanotube funnels 13. The two dimensional multilayered piezoelectric amplifier structure 200 may be an interface structure for a biological environment. In one embodiment, the interface structure to the biological environment may include at least one composite electrical impulse generating layer 20 comprising a matrix phase of a piezo polymer material 5, a first dispersed phase of piezo nanocrystals 10, and a second dispersed phase of carbon nanotube funnels 13, wherein the first and second dispersed phases are present throughout the matrix phase. The piezo polymer material 5 and piezo nanocrystal 10 convert mechanical motion into electrical impulses and accept electrons to charge the composite impulse generating layer 20. The carbon nanotube funnels 13 provide pathways for distribution of the electrical impulses to a transmission surface of the composite impulse generating layer 20, and delivery of byproducts of free radicals degradation from the biological environment to both piezo-nanocrystals 10 and piezo-polymer material 5.

It is noted that in some embodiments, the composite may include a third dispersed phase of linear carbon nanotubes 12. The linear carbon nanotubes 12 may be non-agglomerated, and may be referred to as being discrete.

In some embodiments, carbon nanotube funnels (CNTF) may be mixed with the composite impulse generating layer 20. The mixture of the carbon nanotube funnels (CNTF) in the above described compositions of the composite impulse generating layer 20 provides a new multilayered composite film-like material with more streamlined electron flow from the biological environment interface to the depth of the structure. Carbon nanotube funnels (CNTF) are structures of larger carbon nanotubes with more conical shape (one end is wider than another) that are cup-stacked one into another forming funnels for electrons. Carbon nanotube funnels (CNTF) function as an electron concentrator based on carbon nanoparticle (CNP)-fullerene structure inside polymer piezoelectric layer. The carbon nanotube funnels (CNTF) concentrate the electron flow density.

In some embodiments, the carbon nanotube funnels (CNTF) structures are formed from graphene plates. Further details on one embodiment of carbon nanotube funnels can be found in the publication by Xiaolin Zhao et al., *Defect enabled formation of multilayered funnel from isolated graphene nanoring*, Physical Chemistry Chemical Physics, (November 2016) 18(45).

Carbon nanotube funnels (CNTF) can be embedded in the composite electrical impulse amplifying layer 21 and the composite impulse generating layer 20. The wider part of the funnel is faced to biological tissue contact surface; and the narrow part is facing the quantum dots (QD)-embedded glass cylinder. These structures can be polarized at the time of polymerization of the polymer they are embedded into to ensure the orientation somewhat perpendicular to the outer layer. The effective concentration of such funnels in the layers is 0.01-0.01% by weight. In some embodiments, a device may be provided by the multilayered composite film-like material 200 from FIG. 2 wrapped around photovoltaic unit 100 from FIG. 1. In this embodiment the electrons will be collected from neurons via the multilayered material 200, amplified and streamed onto photovoltaic unit 100. Electrons will be further transformed to photons on quantum dots 50, and the resulting light will be transmitted to the light-sensitive and computing devices through fiber optic cable 55. In the opposite direction the photons of the light coming from a light source (coherent LED or laser) will be transformed onto quantum dots 50 into electrons, and the resulting electrons/signals will be further transmitted to the biological environment interface layer 25 to affect juxtapositioned neurons.

The quantum dots (QD)-containing glass optical-electric transducer comprises holey silicon oxide fibers (e.g. with hydrofluoric acid based acid composition) or low melting point glass fibers containing quantum dots. Multiple fibers will be glued together into the cable. The transducer can be manufactured in a shape of a cylinder (for cylindrical or flat-shaped final contraptions) or a sphere (for spherical or irregular 3D contraptions). Base amorphous silicon oxide material consists of a holey optical fiber having a plurality of holes that provide light confinement. A plurality of quantum dots are disposed within the holes. The quantum dots provide photon-to-electron and electron-to-photon conversion. The wavelength conversion, amplification, fluorescence, absorption, lasing and other linear and non-linear light functions are dependent on the individual quantum dot composition and the parameters of light or electrons it absorbs in any given time. In case of electron-to-photon conversion the resulting light will be passed to the optic fiber to the light-sensing electronic and computing devices.

Quantum dots (QDs) 50 are three-dimensionally confined semiconductor nanocrystals. Colloidal quantum dots based on Telurid or Selenid (PbSe or CdSe and PbTe or CdTe particle high crystals 27 nm). In some embodiments, the quantum dots (QD) 50 have a composition that may be PbSe/CdSe and PbTe/CdTe in crystals. The quantum dot (QD) size may be a single 2 nm$^3$ crystal that contains approximately 200 atoms. In another embodiment, the quantum dot (QD) size is an 8 nm$^3$ crystal that contains about 10,000 atoms. In yet another embodiment, the quantum dot (QD) size ranges from 25-50 nm.

The quantum dots (QDs) 50 function is to harvest a fixed amount of energy from photon and transduce it into electrons, and, in other direction, to harvest energy from an electron and transduce it into a photon due to photovoltaic phenomenon. The solar spectrum consists of photons with energies ranging 0.4 eV to 4.0 eV. The band-gap of the semiconductor determines how much solar energy can be converted to electrical power. The quantum dots 50 provide a wavelength specific conversion of photons to electrons and back.

The optical fibers 55 are used to transmit light a light source (laser or coherent light emitting LED) and QD-containing material in one direction, and QD-containing material 50 and a light sensor in the opposite direction. Optical fibers 55 are made of plastic or by silica glass drawing. Optic fiber measurements: diameter 0.5 nanometers to 10 nanometers; length up to 20 cm. Optical fibers 55 are to be assembled into a cable with the diameter starting from 1 mm. The optical fibers 55 may be made of glass and having quantum dots 50 embedded in the glass.

The optical fibers 55 can be flexible, transparent fiber made by drawing glass (silica) or plastic. Projected diameter of a single fiber 0.5 nm to 1 nm. Optical fibers can transmit light signals between the holey optical nano-porous glass with quantum dots fibers and a source of coherent light, and between electronic devices. Commercially available lasers or LED with various wavelength of emitting light can provide a coherent light source.

A holey optical fiber 55 can be made of nano-porous glass and can have a plurality of holes that provide light confinement. A holey optical fiber 55 represents amorphous glass with nano-pores in which quantum dots 55 are confined. The available glass options for forming the holey optical fiber 55 can include borosilicate glasses, phosphate glasses, and lead-containing glasses. In some embodiments, a holey optical nano-porous glass fiber 55 can be formed by being submerged in a colloid or suspension of quantum dots 50 in a solvent. The quantum dots are drawn into the holes by capillary action.

Figure 4:
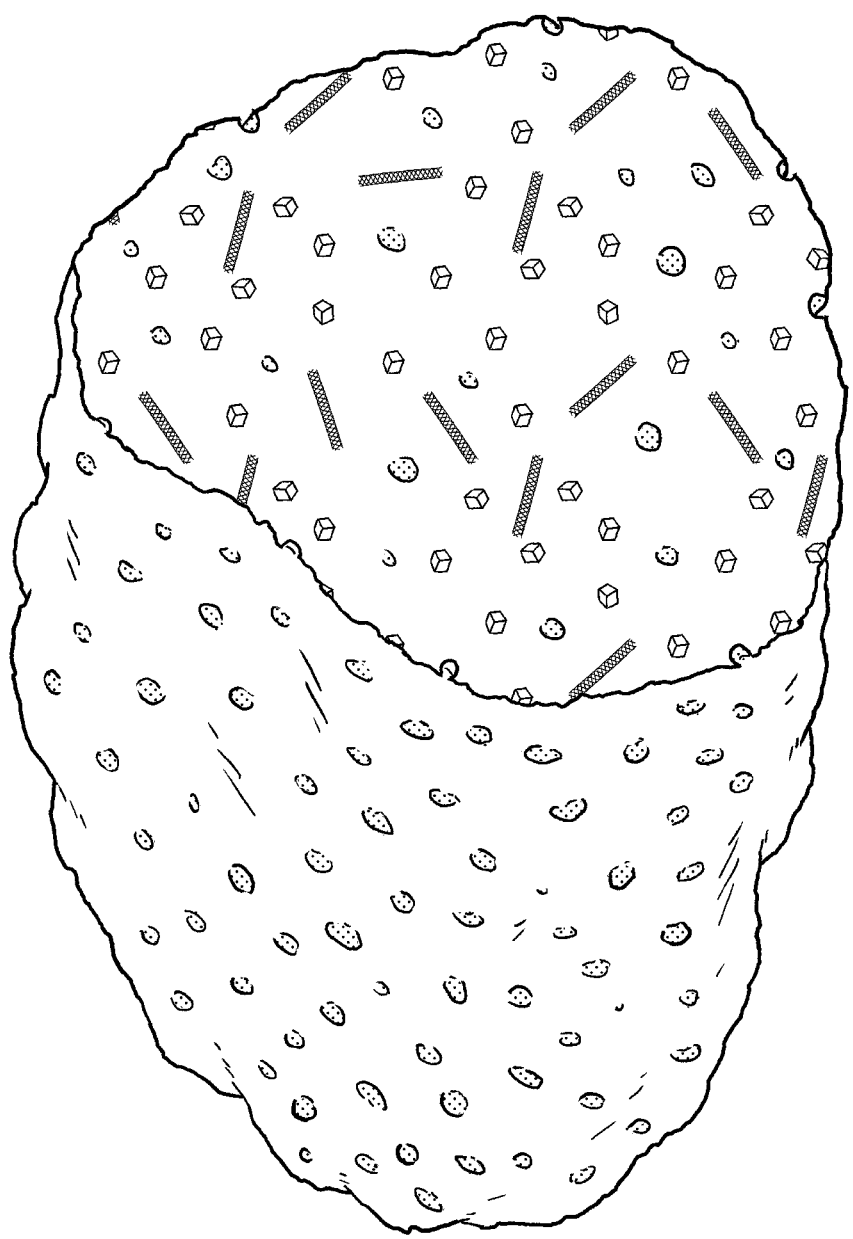
FIG. 4 is a first embodiment of a three dimension sponge used to send and receive signals, in which the photovoltaic unit depicted in FIG. 1 is integrated into the sponge configuration depicted in FIG. 4.

Other form factors for the devices provided herein have been described in the patent U.S. patent application Ser. No. 15/883,793. FIG. 4 is a first embodiment of a three dimension sponge used a form factor to send and receive signals, in which the photovoltaic unit depicted in FIG. 1 is integrated into the sponge configuration depicted in FIG. 4. FIG. 5 is a second embodiment of a three dimension sponge used as a form factor to send and receive signals, in which the photovoltaic unit depicted in FIG. 1 is integrated into the sponge configuration depicted in FIG. 4. The compositions for each of the form factors included in FIGS. 4 and 5 may include or may not include carbon nanotube funnels (CNTF). The resulting embodiment will receive electrons from neurons, amplified and streamed onto photovoltaic unit. Electrons will be further transformed to photons on quantum dots, and the resulting light will be transmitted to the light-sensitive and computing devices through fiber optic cable 55.

FIG. 4 depicts a multilayered composite material utilizing quantum dot based photovoltaic effect for bi-directional brain computer interfaces having a three dimensional form factor in the shape of a sponge. It is noted that the structure in FIG. 4 can be three dimensional. However, the structure depicted in FIG. 4 may also be configured to be flat. FIG. 5 depicts a multilayered composite material utilizing quantum dot based photovoltaic effect for bi-directional brain computer interfaces having a three dimensional form factor in the three dimensional "ink-blot". In some instances, the three dimensional blot interface structure may be referred to as a dendritic geometry. The dendritic geometry can results from the application of an injectable "electrode" in the form of a suspension that polymerizes in the neuron-glial meshwork in situ. In this example, the nano-particles of the piezo-material are to be suspended in the liquid biocompatible polymer composition that promptly polymerizes in the targeted area in the "dendrite-like" distributed fashion and/or fill pathological cavities (e.g. "lacunar microinfarcts"). Such "distributed dendrite-like" electrode will provide an intimate functional bi-directional interface with the cellular membranes. The currently available metal point electrodes are lacking these features.

In one embodiment, the material that provides the sponge and three dimensional blot interface structures may be a composite of piezoelectric materials and carbon nanotubes. In some embodiments, the three dimensional structures depicted in FIGS. 4 and 5 may have CNTF structures present therein. In some embodiments, the CNTF structure may be mixed into the matrix for the sponge and three dimensional blot interface structures. Prior to polymerization, the mixture may be injected into biological tissue. Thereafter, the mixture may be contacted by metal electrodes, and polymerized with an electric field radially. In some embodiments, following polymerization, the metal electrodes may be replaced with fiber optic cables including quantum dots.

In one example, the composite material that provides the sponge and three dimensional blot interface structures 100*i*, 100*g* can include a piezo polymeric material in an amount ranging from 70 wt. % to 95 wt., piezo nanocrystals in an amount ranging from 15 wt. % to 30 wt. % and carbon nanotubes present in an amount ranging from 0.1 wt. % to 1 wt. %. The composite material employed in the interface structures is similar to the composite electrical impulse generating layer 20 and the composite electrical impulse amplifying layer 21. Therefore, the description of the compositions for the piezo polymer matrix 5, the piezo nanocrystals 10 and the carbon nanotubes 15 for the composite electrical impulse generating layer 20 and the composite electrical impulse amplifying layer 21 is suitable for providing at least one example for these materials applied to the interface structures depicted in FIGS. 3 and 4. For example, the piezo polymeric material 5 may be polyvinylidene fluoride trifluoroethylene (PVDF-TrFE).

In another embodiment, the composition of a piezo polymeric material such as polyvinylidene fluoride trifluoroethylene (PVDF-TrFE) for the interface structures depicted in FIGS. 3 and 4 may be substituted with a polymeric material selected for enhanced biocompatibility, such as polyanhydride poly-[bis(p-carboxyphenoxy)propane-sebacic acid] copolymer (PCPP-SA). In some embodiments, the sponge and three dimensional blot interface structures may be porous structures having a pore diameter ranging from 5 μm to 20 μm.

The three dimensional blot interface structure having dendritic geometry depicted in FIG. 5 may be injected into tissue and formed therein from a liquid polymer with suspended piezo-electric nano-crystals. Once injected in tissue (approximate volume 3-5 cubic mm to 1-2 cubic centimeter) the material promptly polymerizes, so the suspended nano-crystals become embedded in (semi-) rigid polymer matrix. The embedded nano-crystals will be positioned in the immediate proximity of the membranes of the excitable elements of the brain, i.e. neurons (soma, axons, and dendrites) as well as of glial cells. We anticipate that these excitable cells will amplify and propagate impulses according to their physiologic properties.

In another aspect, the photovoltaic unit 100 may be employed in a method of interfacing with a biological tissue. In one embodiment, the method of interfacing with the biological tissue may include sensing an electrical signal from the biological tissue with a biological interface 30 including a multilayered piezoelectric amplifier 200 including a composite impulse generating layer 21 including a matrix of a piezo polymeric material 5 and dispersed phases including piezo nanocrystals 10 and carbon nanotubes, e.g., linear carbon nanotubes 12 and/or nanotube funnels 13. In a following step, the method can further include receiving the electrical signal from the biological interface 30 with carbon nanotube funnels 75; and converting the electrical signal to a light signal with a transducer structure. In some embodiments, the transducer structure includes a fiber substrate 50 having quantum dots 55 present on a receiving end of the fiber substrate 50. The receiving end of the fiber receives the electrical signal from the carbon nanotube funnels 75, and the quantum dots 55 providing said converting of the electrical signal to the light signal.

Figure 6:
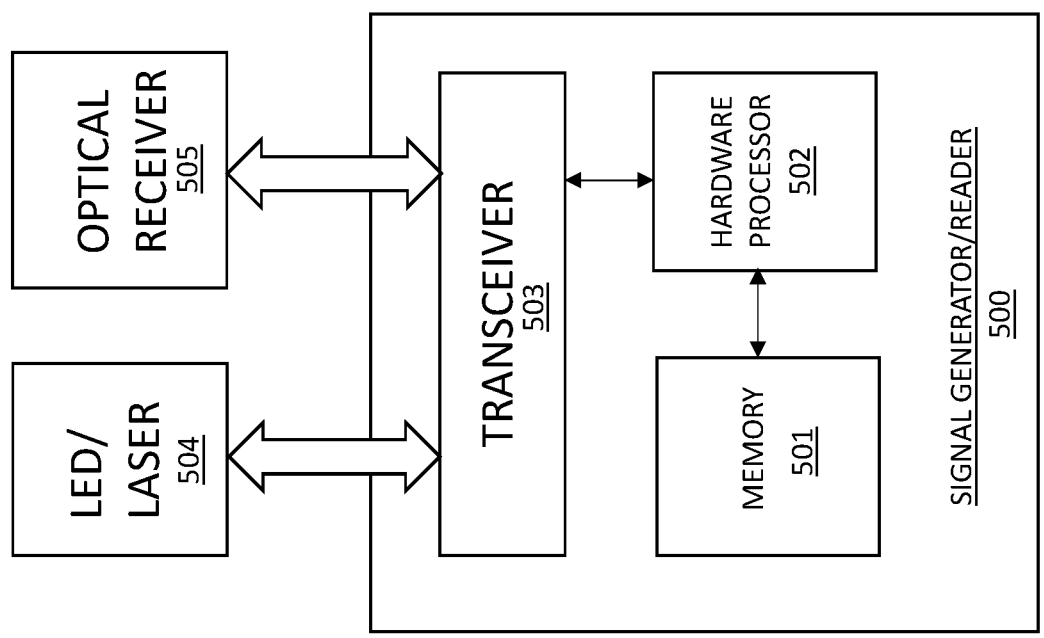
FIG. 6 is a block diagram of a processor system that can function to send and/or receive signals from the photovoltaic unit including a plurality of fiber substrates, e.g., optical fibers, embedded with quantum dots, in accordance with one embodiment of the present disclosure.

In one example, the method of interfacing with the biological tissue may be used in combination with a system for a bi-directional brain-computer interface. FIG. 6 is a block diagram of a signal generator/reader 500 that can function to send and/or receive signals from the photovoltaic unit 100 including a plurality of optical fibers 55 embedded with quantum dots 50. The signal generator/reader 500 may include a transceiver 503 for communicating with a light emitting diode (LED)/laser 504 for sending signals through the photovoltaic unit 100. The transceiver 503 may also provide for communicating with an optical receiver 505 for receiving signals from the photovoltaic unit 100.

The single generator/reader may also include a hardware processor 500 and memory 501 that is configured to actuate a number of commands for analyzing signals received and/or sent for the purposes of identifying a biological phenomena and/or effectuating a treatment related to neuromodulation, neurostimulation, neuroprosthetics, and/or other brain-computer interfaces for deep brain stimulation.

Neurostimulation can be a form of deep brain stimulation (DBS) for Parkinson's disease (PD). Deep brain stimulation (DBS) can be effective as a treatment for variety of neurodegenerative diseases (ND), chronic pain, psychiatric disorders, and dystonias.

The memory 501 may store any type of software having commands to be carried out by the hardware processor 502 interacting with the transceiver 503.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

The memory 501 may be any type of memory, such as hardware memory that can include, but is not limited to random access memory (RAM), a read-only memory (ROM), an erasable programmable read-only memory (EPROM or Flash memory), a static random access memory (SRAM) and combinations thereof.

In some embodiments, the proposed system for the bi-directional brain-computer interface can function to received signals. For example, an electric signal will be sensed from the cellular membrane of a neuron with a biological interface 30 including a multilayered piezoelectric amplifier 200. In some embodiments, the electrical signal is further amplified with the use of the piezo-electric effect, and transported onto the quantum dots 55 of the transducer structure including the optical fiber substrate 55 via carbon nanotube funnels 75. The quantum dots 55 transform the amplified electric signal into light. The characteristics of the light that the quantum dots 55 convert the electrical signal to can at least partially depend on the composition of the particular quantum dot. The resulting light will be further passed to the light sensors and further computing devices, e.g., the signal generator/receiver 500, via the optical fiber substrate 55 for analysis.

In some embodiments, the proposed system for the bi-directional brain-computer interface can function to send signals. In one example, a light signal from a coherent light source, e.g., light emitting diode (LED) light source and/or laser light source 50, can be sent to quantum dots 55 via fiber optics 50, where it will be transformed into electrical signals, in correspondence to the particular quantum dot 55. An electrical signal will be further distributed to the surrounding neurons via the biological interface surface 30, which includes the including a multilayered piezoelectric amplifier 200, through polarized carbon nanotubes. The polarized carbon nanotubes can be provided by the carbon nanotube funnels 75.

Thus, in some embodiments, the proposed system allows a bi-directional interface between brain (neurons) and computing devices. The advanced feature of this system is that offers a high-density multichannel (pixelated surface and various light wave lengths) signal exchange between the brain and a computer, e.g., signal generator/reader 500.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a multilayered composite material utilizing quantum dot based photovoltaic effect for bi-directional brain computer interfaces (which are intended to be illustrative and not limiting), it is noted that modifications and variations can be made by persons skilled in the art in light of the above teachings.

The invention claimed is:

1. A photovoltaic unit comprising:
a biological interface for sensing an electrical signal from the biological tissue, the biological interface including a multilayered piezoelectric amplifier including a composite impulse generating layer including a matrix of a piezo polymeric material and dispersed phases including piezo nanocrystals and carbon nanotubes;
carbon nanotube funnels for receiving the electrical signal from the biological interface, the carbon nanotube funnels having a carbon based structure with a first diameter at a first end of the carbon based structure and a second diameter of an opposing second end of the carbon based structure, wherein the first diameter is greater than the second diameter; and
a transducer structure comprising a fiber substrate having quantum dots present on a receiving end of the fiber, the receiving end of the fiber receiving the electrical signal from the carbon nanotube funnels, the quantum dots converting the electrical signal to a light signal.

2. The photovoltaic unit of claim 1, wherein the composite electrical impulse generating layer may include the piezo polymeric material in an amount ranging from 70 wt. % to 84.9 wt. %; piezo nanocrystals in an amount ranging from 15 wt. % to 30 wt. %; and carbon nanotubes in an amount ranging from 0.1 wt. % to 1 wt. %.

3. The photovoltaic unit of claim 1, wherein the piezo polymer material has a composition that is selected from the group consisting of polyvinylidene flouride (PVDF), polyvinylidene fluoride (PVDF) copolymer with triflourethylene (TrFE), polyvinylidene fluoride (PVDF) copolymer with tetrafluorethylene (TFE), polyvinylidene fluoride (PVDF) copolymer with tetrafluorethylene (TFE) and triflourethylene (TrFE), nylon 11, poly(vinylidenecyanide vinylacetate), and combinations thereof.

4. The photovoltaic unit of claim 1, wherein the piezo nanocrystal is a piezo ceramic material having crystals with a composition selected from the group consisting of lead zirconate ($PbZrO_3$), lead titanate ($PbTiO_3$), and combinations thereof.

5. The photovoltaic unit of claim 1, wherein the quantum dots have a composition selected from the group consisting of telurid, selenid, PbSe, CdSe, PbTe, CdTe and combinations thereof.

6. The photovoltaic unit of claim 1, wherein the fiber structure is an optical fiber comprised of silica ($SiO_2$).

7. A photovoltaic unit comprising:
a biological interface for sensing an electrical signal from the biological tissue, the biological interface including a multilayered piezoelectric amplifier including a composite impulse generating layer including a matrix of a piezo polymeric material and dispersed phases including piezo nanocrystals and carbon nanotubes, wherein the carbon nanotubes of the multilayered piezoelectric amplifier are carbon nanotube funnels;
carbon nanotube funnels for receiving the electrical signal from the biological interface; and
a transducer structure comprising a fiber substrate having quantum dots present on a receiving end of the fiber, the receiving end of the fiber receiving the electrical signal from the carbon nanotube funnels, the quantum dots converting the electrical signal to a light signal.

* * * * *